(12) United States Patent
Kishi et al.

(10) Patent No.: US 9,328,306 B2
(45) Date of Patent: May 3, 2016

(54) MIXED ESTER

(71) Applicant: KH NEOCHEM CO., LTD., Tokyo (JP)

(72) Inventors: Junya Kishi, Mie (JP); Yuichiro Nakai, Chiba (JP); Shinji Tanaka, Mie (JP); Toshihiro Inayama, Mie (JP)

(73) Assignee: KH NEOCHEM CO., LTD., Tokyo (JP)

( * ) Notice: Subject to any disclaimer, the term of this patent is extended or adjusted under 35 U.S.C. 154(b) by 0 days.

(21) Appl. No.: 14/375,645

(22) PCT Filed: Jan. 31, 2013

(86) PCT No.: PCT/JP2013/052137
§ 371 (c)(1),
(2) Date: Jul. 30, 2014

(87) PCT Pub. No.: WO2013/115296
PCT Pub. Date: Aug. 8, 2013

(65) Prior Publication Data
US 2015/0001438 A1    Jan. 1, 2015

(30) Foreign Application Priority Data

Feb. 1, 2012    (JP) ................................. 2012-019802

(51) Int. Cl.
*C09K 5/04* (2006.01)
*C10M 105/38* (2006.01)
*C07C 69/33* (2006.01)
*C10M 171/00* (2006.01)

(52) U.S. Cl.
CPC .............. *C10M 105/38* (2013.01); *C07C 69/33* (2013.01); *C09K 5/041* (2013.01); *C10M 171/008* (2013.01); *C09K 2205/104* (2013.01); *C10M 2207/026* (2013.01); *C10M 2207/2835* (2013.01); *C10N 2220/028* (2013.01); *C10N 2220/302* (2013.01); *C10N 2230/02* (2013.01); *C10N 2230/06* (2013.01); *C10N 2230/10* (2013.01); *C10N 2230/70* (2013.01); *C10N 2240/30* (2013.01)

(58) Field of Classification Search
CPC ........................... C10M 105/34; C10M 105/38
USPC ............................................ 252/68; 508/485
See application file for complete search history.

(56) References Cited

U.S. PATENT DOCUMENTS

| 5,494,597 | A | * | 2/1996 | Krevalis et al. | ................. 252/68 |
| 6,468,319 | B1 | * | 10/2002 | Yeh et al. | ........................ 44/388 |
| 8,318,040 | B2 | | 11/2012 | Sawada et al. | |
| 2002/0137640 | A1 | * | 9/2002 | Memita et al. | ................. 508/485 |
| 2003/0201420 | A1 | * | 10/2003 | Schlosberg et al. | ............. 252/68 |
| 2007/0027244 | A1 | * | 2/2007 | Schar et al. | .................... 524/306 |
| 2010/0038582 | A1 | | 2/2010 | Shimomura et al. | |
| 2010/0051854 | A1 | | 3/2010 | Sawada et al. | |
| 2011/0247578 | A1 | | 10/2011 | Jansson et al. | |
| 2014/0100149 | A1 | | 4/2014 | Jansson et al. | |

FOREIGN PATENT DOCUMENTS

| CN | 1400293 A | 3/2003 |
| JP | H03-200895 A | 9/1991 |
| JP | H10-158215 A | 6/1998 |
| JP | 2002-129177 A | 5/2002 |
| JP | 3429031 B2 | 7/2003 |
| JP | 2009-074017 A | 4/2009 |
| JP | 2010-090285 A | 4/2010 |
| WO | WO-2008/105366 A1 | 9/2008 |
| WO | WO-2008/117657 A1 | 10/2008 |
| WO | WO-2010/029704 A1 | 3/2010 |
| WO | WO-2010/050871 A1 | 5/2010 |

OTHER PUBLICATIONS

Kobayashi et al., The Correlation and the Measurement of PVTx Properties for New Binary Mixtures Including HFO Refrigerants, Proceedings of JSRAE Annual Conference, Japan Society of Refrigerating and Air Conditioning Engineers, p. 221-224 (2011).
International Bureau of WIPO, International Preliminary Report on Patentability for International Application No. PCT/JP2013/052137, mailed Aug. 6, 2014.
International Searching Authority, International Search Report for International Application No. PCT/JP2013/052137, mailed Apr. 16, 2013.
International Searching Authority, Written Opinion for International Application No. PCT/JP2013/052137, mailed Apr. 16, 2013.
The State of Intellectual Property Office of the People's Republic of China, Notification of First Office Action, issued for Chinese Application No. 201380006816.9, mailed Jun. 1, 2015.

* cited by examiner

*Primary Examiner* — John Hardee
(74) *Attorney, Agent, or Firm* — Marshall, Gerstein & Borun LLP

(57) ABSTRACT

The present invention provides a mixed ester of pentaerythritol or a mixed polyhydric alcohol and carboxylic acids; the mixed polyhydric alcohol consisting of pentaerythritol and dipentaerythritol represented by formula (I), and the carboxylic acids comprising 3,5,5-trimethylhexanoic acid and 2-propylheptanoic acid. The mixed ester exhibits excellent properties (e.g., miscibility with a refrigerant that comprises fluoropropene, low-temperature properties, oxidation stability, oxidation-hydrolysis stability, and lubricity) in a well-balanced manner while having the viscosity within the range required for a refrigerant oil, and may be used in an industrial lubricant (e.g., refrigerant oil) and the like.

6 Claims, No Drawings

MIXED ESTER

TECHNICAL FIELD

The invention relates to a mixed ester that may be used in an industrial lubricant (e.g., refrigerant oil) and the like.

BACKGROUND ART

In recent years, hydrofluorocarbon(s) (HFC) that have ozone depletion potential of zero has been used as a refrigerant for a refrigerator and the like. However, since the HFC still have high global warming potential (GWP), a refrigerant that has lower GWP has been desired. At present, fluoropropene refrigerants such as 2,3,3,3-tetrafluoro-1-propene (hereinafter referred to as "HFO-1234yf") and 1,3,3,3-tetrafluoro-1-propene (hereinafter referred to as "HFO-1234ze"); a mixed refrigerant of fluoropropene and HFC; and the like have been considered to be candidates for such a refrigerant (see Patent Document 1 and Non-patent Document 1).

A refrigerator is normally configured so that a refrigerant oil circulates through the refrigerant circulation cycle together with a refrigerant that lubricates a refrigerant compressor. Therefore, the refrigerant oil is required to have miscibility with the refrigerant. Since the refrigerant oil is used to lubricate the operational parts of the refrigerator, it is important for the refrigerant oil to also have lubricity. When the refrigerant oil undergoes phase separation, the refrigerant oil discharged from the refrigerant compressor may easily remain within the cycle. As a result, the amount of the refrigerant oil in the refrigerant compressor may decrease and a lubrication failure may occur, and/or an expansion mechanism (e.g., capillary) may be clogged. It is important to retain the oil film inside the compressor with high operating temperature in order to implement lubricity inside the refrigerator, and the viscosity of the refrigerant oil is an important factor for retaining the oil film. If the viscosity of the refrigerant oil is low, the thickness of the oil film may decrease, and a lubrication failure may occur. If the viscosity of the refrigerant oil is high, the heat exchange efficiency may decrease (see Patent Documents 2 and 3).

An industrial lubricant such as a refrigerant oil is normally required to have excellent low-temperature properties for use in a low-temperature environment (e.g., winter or a cold district) and also to have improved stability. Examples of the stability include thermal stability, oxidation stability, oxidation-hydrolysis stability, and the like. An apparatus that utilizes the lubricant is required to have improved durability (e.g., wear resistance and fatigue resistance), improved energy-saving capability, and the like.

Patent Document 4 discloses a refrigerant oil that consists of a tetraester of pentaerythritol and 3,5,5-trimethylhexanoic acid. However, the ester disclosed in Patent Document 4 has unsatisfactory low-temperature properties, oxidation-hydrolysis stability, and the like. Patent Document 4 does not disclose or suggest the miscibility of the ester with a refrigerant that comprises fluoropropene.

Patent Document 5 discloses a lubricant base stock for an automotive/aeronautic engine/turbine and the like that comprises a tetraester of 2-propylheptanoic acid and pentaerythritol. Patent Document 5 does not disclose or suggest the miscibility of the ester with a refrigerant that comprises fluoropropene.

Patent Document 6 discloses a refrigerant oil that comprises an ester of a mixed fatty acid and pentaerythritol, wherein the mixed fatty acid consists of Fatty Acid B, which comprises 98.0 mol % of branched fatty acids having 10~13 carbon atoms, and 3,5,5-trimethylhexanoic acid. However, Patent Document 6 does not disclose a specific component of the branched fatty acid having 10 carbon atoms. Patent Document 6 does not disclose or suggest the miscibility of the ester with a refrigerant that comprises fluoropropene.

Patent Document 1 discloses a refrigerant oil that comprises an ester of pentaerythritol and a mixed fatty acid that consists of 2-ethylhexanoic acid and 3,5,5-trimethylhexanoic acid (mixing ratio (molar ratio): 50/50), and discloses the miscibility of the ester with HFO-1234yf at 0° C. Patent Document 7 discloses the pour point of the ester. However, the lubricity and the like of the ester are unsatisfactory, and the performance required for an industrial lubricant (e.g., refrigerant oil) and the like is not achieved in a well-balanced manner.

RELATED-ART DOCUMENT

Patent Documents

Patent Document 1: JP 2009-74017 A
Patent Document 2: JP 2002-129177 A
Patent Document 3: JP 3429031 B
Patent Document 4: JP H03-200895 A
Patent Document 5: WO 2010/050871 A1
Patent Document 6: WO 2008/117657 A1
Patent Document 7: JP 2010-90285 A

Non-Patent Document

Non-patent Document 1: Proceedings of 2011 JSRAE annual conference, Japan Society of Refrigerating and Air Conditioning Engineers, p. 221

SUMMARY OF THE INVENTION

Technical Problem

An object of the invention is to provide a mixed ester that exhibits excellent properties (e.g., miscibility with a refrigerant that comprises fluoropropene, low-temperature properties, oxidation stability, oxidation-hydrolysis stability, and lubricity) in a well-balanced manner while having the viscosity within the range required for a refrigerant oil, and may be used in an industrial lubricant (e.g., refrigerant oil) and the like.

Solution to Problem

Several aspects of the invention provide the following.
[1] A mixed ester of pentaerythritol or a mixed polyhydric alcohol and carboxylic acids; the mixed polyhydric alcohol consisting of pentaerythritol and dipentaerythritol represented by the following formula (I), and the carboxylic acids comprising 3,5,5-trimethylhexanoic acid and 2-propylheptanoic acid.

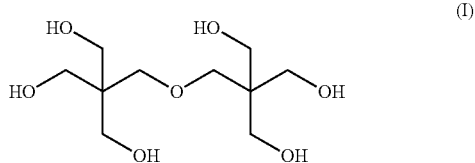 [SMILES: OCC(CO)(CO)COCC(CO)(CO)CO]
(I)

[2] The mixed ester according to [1], wherein the carboxylic acids consist of 3,5,5-trimethylhexanoic acid and 2-propylheptanoic acid.

[3] The mixed ester according to [1] or [2], wherein the carboxylic acids comprise 3,5,5-trimethylhexanoic acid and 2-propylheptanoic acid in a molar ratio of 90/10 to 10/90.

[4] The mixed ester according to any one of [1] to [3], wherein the polyhydric alcohol that forms the mixed ester is pentaerythritol.

[5] A refrigerant oil comprising the mixed ester according to any one of [1] to [4].

[6] A working fluid composition for refrigerator comprising the refrigerant oil according to [5] and a refrigerant.

Advantageous Effects of the Invention

The invention thus provides a mixed ester that exhibits excellent properties (e.g., miscibility with a refrigerant that comprises fluoropropene, low-temperature properties, oxidation stability, oxidation-hydrolysis stability, and lubricity) in a well-balanced manner while having the viscosity within the range required for a refrigerant oil, and may be used in an industrial lubricant (e.g., refrigerant oil) and the like.

DESCRIPTION OF EMBODIMENTS

The mixed ester according to the invention is a mixed ester of pentaerythritol and carboxylic acids that comprise 3,5,5-trimethylhexanoic acid and 2-propylheptanoic acid; or a mixed ester of a mixed polyhydric alcohol and carboxylic acids, wherein the mixed polyhydric alcohol consists of pentaerythritol and dipentaerythritol represented by the following formula (I), and wherein the carboxylic acids comprise 3,5,5-trimethylhexanoic acid and 2-propylheptanoic acid.

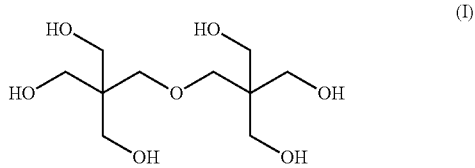 [SMILES: OCC(CO)(CO)COCC(CO)(CO)CO]

(I)

The term "mixed ester" used herein refers to a compound obtained by esterification using a plurality of kinds of carboxylic acids that form an ester together with polyhydric alcohol(s).

Hereinafter, pentaerythritol or the mixed polyhydric alcohol that consists of pentaerythritol and dipentaerythritol which forms the mixed ester according to the invention is referred to as "constituent alcohol(s)", and the carboxylic acid(s) which form the mixed ester according to the invention are referred to as "constituent carboxylic acid(s)".

The mixed ester according to the invention includes (i) a mixed ester of the constituent carboxylic acids and the constituent alcohol(s), wherein the constituent carboxylic acids in one molecule comprise both 3,5,5-trimethylhexanoic acid and 2-propylheptanoic acid; (ii) a mixture of an ester of the constituent alcohol(s) and the constituent carboxylic acid(s) that comprise 3,5,5-trimethylhexanoic acid, and an ester of the constituent alcohol(s) and the constituent carboxylic acid(s) that comprise 2-propylheptanoic acid; and (iii) a mixture of (i) and (ii).

The mixed ester according to the invention may comprise a partial ester in which some of the hydroxyl groups of the constituent alcohol(s) remain unesterified as impurities.

The constituent carboxylic acid(s) may comprise additional carboxylic acid(s) other than 3,5,5-trimethylhexanoic acid and 2-propylheptanoic acid. Examples of the additional carboxylic acid include linear aliphatic monocarboxylic acids (e.g., acetic acid, propionic acid, hexanoic acid, peptane acid, octanoic acid, nonanoic acid, dodecanoic acid, tetradecanoic acid, hexadecanoic acid, and octadecanoic acid), branched aliphatic monocarboxylic acids (e.g., 2-ethylbutyric acid, 2-methylpentanoic acid, 4-methylpentanoic acid, 2-methylhexanoic acid, 2-ethylpentanoic acid, 2-ethyl-2-methylbutyric acid, 2,2-dimethylpentanoic acid, 2-methylheptanoic acid, 3-ethylhexanoic acid, 2-ethyl-2-methylpentanoic acid, 2-methyloctanoic acid, 2,2-dimethylheptanoic acid, isotridecanoic acid, and isostearic acid), and the like.

The content of the additional carboxylic acid(s) in the constituent carboxylic acid(s) may be in a range without impairing the excellent properties (e.g., miscibility with a refrigerant that comprises fluoropropene, low-temperature properties, oxidation stability, oxidation-hydrolysis stability, and lubricity) of the mixed ester according to the invention while having the viscosity within the range required for a refrigerant oil.

The total content of 3,5,5-trimethylhexanoic acid and 2-propylheptanoic acid in the constituent carboxylic acids is preferably 50 mol % or more, more preferably 80 mol % or more, and still more preferably 90 mol % or more. It is most preferable that the constituent carboxylic acids consist of 3,5,5-trimethylhexanoic acid and 2-propylheptanoic acid.

The molar ratio of 3,5,5-trimethylhexanoic acid to 2-propylheptanoic acid (i.e., 3,5,5-trimethylhexanoic acid/2-propylheptanoic acid) is preferably 90/10 to 10/90, more preferably 90/10 to 15/85, and still more preferably 80/20 to 30/70, from the viewpoint of the viscosity within the range required for a refrigerant oil, miscibility with a refrigerant that comprises fluoropropene, low-temperature properties, oxidation stability, oxidation-hydrolysis stability, and the like. The content of 2-propylheptanoic acid in the constituent carboxylic acids is preferably 10 mol % or more.

When the constituent alcohol(s) are the mixed polyhydric alcohol that consists of pentaerythritol and dipentaerythritol, the content of dipentaerythritol in the constituent alcohol(s) is preferably 30 mol % or less, and more preferably 20 mol % or less, from the viewpoint of the viscosity within the range required for a refrigerant oil, miscibility with a refrigerant that comprises fluoropropene, low-temperature properties, and the like. It is still more preferable that the constituent alcohol includes only pentaerythritol from the viewpoint of the viscosity within the range required for a refrigerant oil, miscibility with a refrigerant that comprises fluoropropene, low-temperature properties, and the like.

As for the mixed polyhydric alcohol that consists of pentaerythritol and dipentaerythritol that forms the mixed ester according to the invention; a commercial product may be used, or it may be prepared by mixing commercially available pentaerythritol and commercially available dipentaerythritol.

2-Propylheptanoic acid that forms the mixed ester according to the invention may be produced in accordance with a known method (e.g., the method disclosed in JP H08-109299 A): by subjecting valeraldehyde to Aldol condensation in the presence of an alkali catalyst to obtain an unsaturated aldehyde, hydrogenating the double bond of the unsaturated aldehyde, and oxidizing the resulting product. 2-Propylheptanoic acid that forms the mixed ester according to the invention may also be produced by dimerizing pentene, and oxidizing the resulting product (see DE10239134), for example.

The mixed ester according to the invention may be produced by reacting the constituent alcohol(s), 3,5,5-trimethylhexanoic acid, 2-propylheptanoic acid, and optionally additional carboxylic acid(s), at 120 to 300° C. for 5 to 60 hours, for example. In this case, all of the carboxylic acids may be added simultaneously, or each of the carboxylic acids may be added successively. For example, all of the carboxylic acids may be mixed, and reacted with the constituent alcohol(s) (Production Method 1); or the constituent alcohol(s), 2-propylheptanoic acid, and optionally additional carboxylic acid(s) may be reacted in specific amounts, and 3,5,5-trimethylhexanoic acid may be successively added to the mixture to react with them (Production Method 2).

Since 2-propylheptanoic acid has a low reaction rate with the constituent alcohol(s), it may relatively take time to produce a mixed ester of the constituent alcohol(s) and carboxylic acids that comprise 2-propylheptanoic acid. However, it is possible to reduce the time required to produce the mixed ester according to the invention by appropriately selecting Production Method 1 or 2 in accordance with the ratio of 3,5,5-trimethylhexanoic acid to 2-propylheptanoic acid in the constituent carboxylic acids. Specifically, when the constituent alcohol is pentaerythritol, and the molar ratio of 3,5,5-trimethylhexanoic acid to 2-propylheptanoic acid (3,5,5-trimethylhexanoic acid/2-propylheptanoic acid) is 30/70 to 95/5, the mixed ester according to the invention can be produced within a relatively short time using Production Method 1 or 2. When the constituent alcohol is pentaerythritol, and the molar ratio of 3,5,5-trimethylhexanoic acid to 2-propylheptanoic acid (3,5,5-trimethylhexanoic acid/2-propylheptanoic acid) is 5/95 to 30/70 (excluding 30/70), the mixed ester according to the invention can be produced within a relatively short time (e.g., 25 hours or less) by selecting Production Method 2. Therefore, the mixed ester according to the invention can be produced with high productivity.

The properties (e.g., miscibility with a refrigerant that comprises fluoropropene, low-temperature properties, oxidation stability, oxidation-hydrolysis stability, and lubricity) of the mixed ester according to the invention are not impaired when the mixed ester is produced using Production Method 1 or 2.

Catalyst(s) may be used during the reaction for producing the mixed ester according to the invention. Examples of the catalyst include mineral acids, organic acids, Lewis acids, organometals, solid acids, and the like. Specific examples of the mineral acids include hydrochloric acid, hydrofluoric acid, sulfuric acid, phosphoric acid, nitric acid, and the like. Specific examples of the organic acids include p-toluenesulfonic acid, benzenesulfonic acid, butanesulfonic acid, propanesulfonic acid, ethanesulfonic acid, methanesulfonic acid, and the like. Specific examples of the Lewis acids include boron trifluoride, aluminum chloride, tin tetrachloride, titanium tetrachloride, and the like. Specific examples of the organometals include tetrapropoxytitanium, tetrabutoxytitanium, tetrakis(2-ethylhexyloxy)titanium, and the like. Specific examples of the solid acids include a cation-exchange resin and the like.

It is preferable to carry out the reaction while removing water produced during the reaction from the reaction mixture.

The sum of the amount (mol) of 3,5,5-trimethylhexanoic acid, the amount (mol) of 2-propylheptanoic acid, and the amount (mol) of additional carboxylic acid(s) is preferably 1.1 to 1.4 times larger than the amount (mol) of the hydroxyl groups of the constituent alcohol(s).

Solvent(s) may be used during the reaction. Examples of the solvent include hydrocarbon-based solvents (e.g., benzene, toluene, xylene, hexane, heptane, isohexane, isooctane, isononane, and decane) and the like.

The molar ratio of 3,5,5-trimethylhexanoic acid to 2-propylheptanoic acid in the resulting mixed ester may differ from the molar ratio of 3,5,5-trimethylhexanoic acid to 2-propylheptanoic acid used to produce the mixed ester, due to the difference in reactivity between 3,5,5-trimethylhexanoic acid and 2-propylheptanoic acid with respect to the constituent alcohol(s).

After completion of the reaction, the resulting mixed ester may optionally be purified using a method (e.g., washing with water and/or an alkaline aqueous solution; treatment with activated carbon, an adsorbent, and the like; chromatography; or distillation) that is normally used in synthetic organic chemistry.

Since the mixed ester according to the invention includes 3,5,5-trimethylhexanoic acid and 2-propylheptanoic acid as the constituent carboxylic acids, the mixed ester exhibits excellent properties (e.g., miscibility with a refrigerant that comprises fluoropropene, viscosity-temperature properties, low-temperature properties, stability, and lubricity) and sufficient properties (e.g., low-temperature fluidity and electrical insulating properties) in a well-balanced manner while having the viscosity within the range required for a refrigerant oil. The mixed ester according to the invention provides excellent lubricity to the refrigerator oil and the working fluid composition for refrigerator according to the invention.

When using the mixed ester according to the invention in a refrigerant oil, it is important for the refrigerant oil to have sufficient lubricity (e.g., friction-reducing capability and wear-reducing capability (antiwear properties)). The lubricity of a refrigerant oil is normally affected by the viscosity of the refrigerant oil. If the viscosity of the refrigerant oil is too low, the thickness of the oil film in the sliding portion may decrease and the amount of wear may increase. As a result, the lifetime of an apparatus and the like for which the lubricant is used tends to decrease. If the viscosity of the refrigerant oil is too high, the viscous resistance may increase and the friction coefficient may increase. As a result, the energy efficiency tends to decrease. Therefore, the mixed ester is required to have the viscosity within the range required for a refrigerant oil.

When using the mixed ester according to the invention in a refrigerant oil, it is important for the mixed ester to have miscibility with a refrigerant. If the mixed ester has insufficient miscibility with a refrigerant, the refrigerant and the refrigerant oil may undergo phase separation, and the refrigerant oil discharged from the refrigerant compressor may remain within the refrigerant circulation cycle, whereby a lubrication failure may occur in the refrigerant compressor. When using the mixed ester according to the invention in a refrigerant oil for which antiwear properties are required for a longer time (e.g., a refrigerant oil used for an air conditioner), the viscosity (refrigerant solution viscosity) of a mixture of the refrigerant and the refrigerant oil may decrease in the refrigerant circulation cycle if the mixed ester has too high miscibility with the refrigerant, and the thickness of the oil film in the sliding portion may decrease, whereby a lubrication failure may occur. A decrease in refrigerant solution viscosity may also result in a decrease in sealing properties of the refrigerant in the sliding portion of the refrigerant compressor. Therefore, the mixed ester is required to have the miscibility within the range required for a refrigerant oil.

The miscibility with a refrigerant is normally evaluated using the two-phase separation temperature. It is considered that the miscibility with a refrigerant at a low temperature side is good when the two-phase separation temperature is low. When using the mixed ester according to the invention in a refrigerant oil, the mixed ester is required to have the two-phase separation temperature (that indicates the degree of miscibility) within the range required for a refrigerant oil. In case that the mixed ester according to the invention is used in a refrigerant oil, the two-phase separation temperature of a mixture of the mixed ester (10%) and a refrigerant that comprises fluoropropene, for example, is preferably −10° C. or lower, and more preferably −10 to −50° C. The miscibility with a refrigerant has a correlation with the properties of the mixed ester.

The viscosity-temperature properties refer to a change in kinematic viscosity with respect to a change in temperature of an oil solution (e.g., lubricant). An oil solution that exhibits excellent viscosity-temperature properties shows a small change in viscosity with respect to a change in temperature. An oil solution that exhibits poor viscosity-temperature properties shows a rapid increase in viscosity at a low temperature region, or shows a significant decrease in kinematic viscosity at a high temperature region. The viscosity-temperature properties are normally indicated by the viscosity index. It is considered that the viscosity-temperature properties are good when the viscosity index is high. The viscosity properties at a low temperature region are referred to as low-temperature fluidity, and indicated by pour point, freezing point, channel point, and the like.

The term "pour point" used herein refers to the lowest temperature at which an oil solution (e.g., lubricant) flows when the oil solution is cooled in accordance with the method specified in the Japanese Industrial Standards (JIS) K 2269. An oil solution having a low pour point is preferable in the point that an operation failure of an apparatus that utilizes the oil solution does not occur, since the oil solution does not show a deterioration in fluidity even when subjected to a low-temperature environment (e.g., winter or a cold distinct).

When storing or using an oil solution (e.g., lubricant) for a long time in a place where the temperature changes to a large extent, it is preferable that the oil solution does not show volatility and the like at a high-temperature region, and does not show solidification, precipitation, and the like at a low-temperature region. The temperature range is not particularly limited. It is preferable that the oil solution can be stably used within the temperature range of about −20° C. to about 150° C. The term "low-temperature properties" used herein means that solidification and precipitation do not occur at a low temperature region.

The term "stability" used in connection with lubricant applications includes thermal stability, oxidation stability, oxidation-hydrolysis stability, shear stability, and the like.

The term "electrical insulating properties" used herein is indicated by the volume resistivity, and are measured in accordance with the method specified in JIS C 2101. When a motor and the like is used in an oil solution (e.g., lubricant), the oil solution is required to have good electrical insulating properties.

The term "lubricity" used herein refers to friction-reducing capability, wear-reducing capability (antiwear properties), extreme-pressure properties, and the like. In a refrigerant circulation cycle, a refrigerant is normally present together with a refrigerant oil in a sliding portion. Therefore, when using the mixed ester according to the invention in a refrigerant oil or a working fluid composition for refrigerator, the mixed ester is required to have excellent lubricity in the presence of a refrigerant (e.g., a refrigerant that comprises fluoropropene).

When using the mixed ester according to the invention in a refrigerant oil, it is preferable that the mixed ester have kinematic viscosity at 40° C. of 20 to 150 mm$^2$/sec, more preferably 30 to 110 mm$^2$/sec, and still more preferably 60 to 110 mm$^2$/sec.

In case that the mixed ester according to the invention is used in a refrigerant oil, if a large amount of hydroxyl groups remains in the mixed ester, undesirable phenomena of the refrigerant oil (e.g., cloudiness at a low temperature, clogging of the capillary device in the refrigerating cycle) may occur. Therefore, it is preferable that the mixed ester have a hydroxyl value of 10 mg KOH/g or less, and more preferably 5 mg KOH/g or less.

The refrigerant oil according to the invention comprises the mixed ester according to the invention. For example, the refrigerant oil may consist only of the mixed ester, or may consist of the mixed ester and additional lubricant base oil(s). The refrigerant oil may optionally further comprise lubricant additive(s). The refrigerant oil comprises the mixed ester as a lubricant base oil.

Examples of the lubricant additive include a detergent-dispersant additive, an antioxidant, a wear-reducing agent (e.g., anti-wear agent, anti-seize agent, and extreme pressure agent), a friction modifier, an oiliness agent, an acid scavenger, a metal deactivator, a rust preventive agent, a pour-point depressant, a viscosity index improver, a thickener, an anti-foaming agent, and the like. The content of each additive in the refrigerant oil is preferably 0.001 to 5 wt %.

Examples of the antioxidant include di-tert-butyl-p-cresol and the like. Examples of the wear-reducing agent include tricresyl phosphate, triphenyl phosphate, and the like. Examples of the acid scavenger include 2-ethylhexyl glycidyl ether, neodecyl glycidyl ester, bis(dibutylphenyl)carbodiimide, and the like. Examples of the metal deactivator include benzotriazole and the like. Examples of the anti-foaming agent include dimethylsiloxane and the like.

Examples of the additional lubricant base oil include a mineral oil, a synthetic base oil, and the like.

Examples of the mineral oil include a paraffinic crude oil, an intermediate base crude oil, a naphthenic base crude oil, and the like. A refined oil obtained by purifying any of said mineral oils via distillation and the like may also be used.

Examples of the synthetic base oil include poly-α-olefins (e.g., polybutene, polypropylene, and α-olefin oligomers having 8 to 14 carbon atoms), aliphatic esters other than the mixed ester according to the invention (e.g., fatty acid monoesters, fatty acid esters of polyhydric alcohols, and aliphatic polybasic acid esters), aromatic esters (e.g., aromatic monoesters, aromatic esters of polyhydric alcohols, and aromatic polybasic acid esters), polyalkylene glycols, polyvinyl ethers, polycarbonates, alkylbenzenes, and the like.

The content of the additional lubricant base oil(s) in the refrigerant oil is not particularly limited as long as various properties (e.g., miscibility with a refrigerant that comprises fluoropropene, low-temperature fluidity, and lubricity) are not impaired while having the viscosity within the range required for a refrigerant oil. The content of the additional lubricant base oil(s) in the refrigerant oil is preferably 70 wt % or less, more preferably 50 wt % or less, still more preferably 40 wt % or less, and most preferably 30 wt % or less.

The working fluid composition for refrigerator according to the invention comprises the refrigerant and the refrigerant oil according to the invention. The mixed ester according to the invention is used in the refrigerant oil that is comprised in the working fluid composition for refrigerator. The refrigerant oil according to the invention and the refrigerant may be mixed in an arbitrary ratio. It is preferable to use the mixed ester according to the invention in an amount of 1 to 1000 parts by weight, and more preferably 2 to 800 parts by weight, based on 100 parts by weight of the refrigerant.

The refrigerant included in the working fluid composition for refrigerator is preferably a refrigerant that comprises at least one compound selected from fluoropropene, a hydrocarbon having 3 to 5 carbon atoms, and carbon dioxide, from the viewpoint of ensuring low GWP and miscibility within the required range. Among them, a refrigerant that comprises fluoropropene is more preferable. Examples of the refrigerant that comprises fluoropropene include a refrigerant that consists only of fluoropropene, a mixed refrigerant that consists of fluoropropene and hydrofluorocarbon(s) (e.g., difluoromethane (hereinafter referred to as "HFC-32")), and the like. Examples of the refrigerant that consists only of fluoropropene include HFO-1234ze, HFO-1234yf, a mixture thereof, and the like. Among them, HFO-1234ze or HFO-1234yf is preferable.

Examples of the mixed refrigerant that consists of fluoropropene and hydrofluorocarbon(s) (e.g., HFC-32) include HFO-1234ze/HFC-32 (i.e., a mixed refrigerant that consists of HFO-1234ze and HFC-32), HFO-1234yf/HFC-32 (i.e., a mixed refrigerant that consists of HFO-1234yf and HFC-32), and the like. Among them, HFO-1234ze/HFC-32 is preferable. The mixing ratio of fluoropropene and hydrofluorocarbon(s) is not particularly limited.

The mixed ester according to the invention may be used in an engine oil, a gear oil, a motor oil used for a hybrid vehicle or an electric vehicle, grease, a cleaning agent for metal parts, a plasticizer, and the like, in addition to the refrigerant oil and the working fluid composition for refrigerator. The refrigerant oil and the working fluid composition for refrigerator according to the invention may preferably be used for a room air conditioner; a packaged air conditioner; an automotive air conditioner; a dehumidifier; a refrigerator; a freezer; a refrigerator-freezer; a vending machine; a showcase; a refrigerator installed, for example, in a chemical plant; and the like.

EXAMPLES

The invention is further described below by way of production examples, examples, comparative examples, and test examples. However, the invention is not limited to the following examples.

The nuclear magnetic resonance spectrum was measured using the following measurement instrument and measurement method.
Measurement instrument: GSX-400 (400 MHz) manufactured by JEOL Ltd.
Measurement method: $^1$H-NMR (standard substance: tetramethylsilane, solvent: $CDCl_3$)

The nuclear magnetic resonance spectrum of the mixed esters produced in Examples 1 to 8 was measured, and the molar ratio of 3,5,5-trimethylhexanoic acid to 2-propylheptanoic acid in the mixed ester was calculated by the following expression.

3,5,5-Trimethylhexanoic acid/2-Propylheptanoic
acid=Integral value of peak $A$/(Integral value of
peak $B$−Integral value of peak $A$)

In the above expression, the peak A corresponds to the peak of one hydrogen atom at the higher magnetic-field-side among the peaks of the hydrogen atoms on the methylene group at the α-position of the carbonyl group of 3,5,5-trimethylhexanoic acid; and the peak B corresponds to the sum of the peak of one hydrogen atom at the lower magnetic-field-side among the peaks of the hydrogen atoms on the methylene group at the α-position of the carbonyl group of 3,5,5-trimethylhexanoic acid, and the peak of one hydrogen atom on the methine group at the α-position of the carbonyl group of 2-propylheptanoic acid.

The molar ratio of pentaerythritol to dipentaerythritol in the mixed esters produced in Examples 7 and 8 was calculated by the following expression.

Pentaerythritol/Dipentaerythritol=(Integral value of
peak $C$/8)/(Integral value of peak $D$/4)

In the above expression, the peak C corresponds to the peak of the eight hydrogen atom on the methylene groups of pentaerythritol; and the peak D corresponds to the peak of the four hydrogen atoms on the methylene group of dipentaerythritol bonded to the ether oxygen atom.

The nuclear magnetic resonance spectrum of the mixed esters produced in Comparative Example 3 was measured, and the molar ratio of 2-ethylhexanoic acid to 3,5,5-trimethylhexanoic acid in the mixed ester was calculated by the following expression.

2-Ethylhexanoic acid/3,5,5-Trimethylhexanoic acid=
(Integral value of peak $E$−Integral value of peak
$A$)/(Integral value of peak $A$)

In the above expression, the peak A is the same as defined above; and the peak E corresponds to the sum of the peak of one hydrogen atom at the lower magnetic-field-side among the peaks of hydrogen atoms on the methylene group at the α-position of the carbonyl group of 3,5,5-trimethylhexanoic acid, and the peak of one hydrogen atom on the methine group at the α-position of the carbonyl group of 2-ethylhexanoic acid.

Production Example

Production of 2-propylheptanoic acid (1) Production of 2-propyl-2-heptenal

A reactor equipped with a dropping funnel and a condenser was charged with 20 g (0.5 mol) of sodium hydroxide (manufactured by Kanto Chemical Co., Inc.) and 500 mL of water. 2434 g (28.3 mol) of n-pentanal ("Valeraldehyde" manufactured by Tokyo Chemical Industry Co., Ltd.) was added dropwise to the mixture from the dropping funnel over 3.5 hours while stirring the mixture at 80° C. The mixture was stirred at 95° C. for 2 hours, and the aqueous layer was removed from the reaction product. The reaction product was purified by distillation (b.p.: 70° C./0.7 kPa) to obtain 1930 g of 2-propyl-2-heptenal.

(2) Production of 2-propylheptanal

An autoclave was charged with 420 g of 2-propyl-2-heptenal and 4 g of a 5% Pd carbon powder (water content: 56%, manufactured by N.E. Chemcat Corporation), and the mixture was stirred at 75° C. for 1.5 hours under a hydrogen pressure of 1.5 MPa. The reaction product was filtered through a membrane filter (PTFE, 0.5 μm) to obtain 416 g of 2-propylheptanal.

(3) Production of 2-propylheptanoic acid

A reactor was charged with 0.2 g (0.005 mol) of sodium hydroxide (manufactured by Kanto Chemical Co., Inc.), 1 g of water, and 0.8 g (0.006 mol) of heptanoic acid (manufactured by Kishida Chemical Co., Ltd.), and the mixture was stirred. After the addition of 47 g of 2-propylheptanal, the mixture was bubbled with air at 40° C. for 15 hours. The mixture was stirred at 130° C. for 4 hours with nitrogen bubbling to obtain crude 2-propylheptanoic acid.

Another reactor was charged with 4 g (0.1 mol) of sodium hydroxide (manufactured by Kanto Chemical Co., Inc.), 36 g of water, and 17 g of the crude 2-propylheptanoic acid, and the mixture was stirred. After the addition of 734 g of 2-propylheptanal, the mixture was bubbled with air at 40° C. for 14 hours. The mixture was stirred at 120° C. for 5 hours with nitrogen bubbling to obtain 804 g of crude 2-propylheptanoic acid. 774 g of the crude 2-propylheptanoic acid was purified by distillation (b.p.: 156 to 157° C./0.4 kPa) to obtain 520 g of 2-propylheptanoic acid.

$^1$H-NMR (CDCl$_3$, δ ppm); 0.88 (t, 3H), 0.92 (t, 3H), 1.29-1.50 (m, 10H), 1.58-1.67 (m, 2H), 2.33-2.40 (m, 1H)

Example 1

Production of mixed ester of pentaerythritol with 3,5,5-trimethylhexanoic acid and 2-propylheptanoic acid in molar ratio (3,5,5-trimethylhexanoic acid/2-propylheptanoic acid) of 90/10 (Mixed Ester 1)

A commercially available product "Kyowaad 500" (manufactured by Kyowa Chemical Industry Co., Ltd.) was used as an adsorbent.

A commercially available product "Shirasagi P" (manufactured by Japan EnviroChemicals, Ltd.) was used as activated carbon.

A reactor equipped with a Dean-Stark trap was charged with 110 g (0.8 mol) of pentaerythritol (manufactured by Koei Perstorp, Co., Ltd.), 553 g (3.5 mol) of 3,5,5-trimethylhexanoic acid (manufactured by KH Neochem Co., Ltd.), and 67 g (0.4 mol) of 2-propylheptanoic acid (see the above production example). The mixture was degassed by nitrogen bubbling at room temperature for 30 minutes with stirring under a reduced pressure of 20 kPa.

The mixture was stirred at 184 to 233° C. for 12 hours with nitrogen bubbling under atmospheric pressure. After completion of the reaction, the reaction product was stirred at 164 to 235° C. for 2 hours under a reduced pressure of 0.9 kPa to remove unreacted carboxylic acids from the reaction product. The reaction product was washed at 90° C. for 0.5 hours with 200 mL of an alkaline aqueous solution containing sodium hydroxide (2 fold moles relative to the acid number of the reaction product). The reaction product was then washed with 200 mL of water at 90° C. for 0.5 hours (three times). Next, the reaction product was stirred at 90° C. for 1 hour under a reduced pressure of 0.9 kPa with nitrogen bubbling to dry the reaction product.

After the addition of 4.0 g of the adsorbent (corresponding to 0.7 wt % of the reaction product) and 2.9 g of activated carbon (corresponding to 0.5 wt % of the reaction product), the mixture was stirred at 100° C. for 2 hours with nitrogen bubbling under a reduced pressure of 1.3 kPa. The mixture was then filtered using a filter aid to obtain 516 g of Mixed Ester 1.

Example 2

Production of mixed ester of pentaerythritol with 3,5,5-trimethylhexanoic acid and 2-propylheptanoic acid in molar ratio (3,5,5-trimethylhexanoic acid/2-propylheptanoic acid) of 77/23 (Mixed Ester 2)

Mixed Ester 2 was obtained in the same manner as in Example 1, except that the molar ratio of pentaerythritol, 3,5,5-trimethylhexanoic acid, and 2-propylheptanoic acid (pentaerythritol/3,5,5-trimethylhexanoic acid/2-propylheptanoic acid) was changed to 1/3.36/1.44, and the reaction time was changed to 14 hours.

Example 3

Production of mixed ester of pentaerythritol with 3,5,5-trimethylhexanoic acid and 2-propylheptanoic acid in molar ratio (3,5,5-trimethylhexanoic acid/2-propylheptanoic acid) of 50/50 (Mixed Ester 3)

Mixed Ester 3 was obtained in the same manner as in Example 1, except that the molar ratio of pentaerythritol, 3,5,5-trimethylhexanoic acid, and 2-propylheptanoic acid (pentaerythritol/3,5,5-trimethylhexanoic acid/2-propylheptanoic acid) was changed to 1/2.20/2.60, and the reaction time was changed to 15 hours.

Example 4

Production of mixed ester of pentaerythritol with 3,5,5-trimethylhexanoic acid and 2-propylheptanoic acid in molar ratio (3,5,5-trimethylhexanoic acid/2-propylheptanoic acid) of 34/66 (Mixed Ester 4)

Mixed Ester 4 was obtained in the same manner as in Example 1, except that the molar ratio of pentaerythritol, 3,5,5-trimethylhexanoic acid, and 2-propylheptanoic acid (pentaerythritol/3,5,5-trimethylhexanoic acid/2-propylheptanoic acid) was changed to 1/1.45/3.35, and the reaction time was changed to 17 hours.

Example 5

Production of mixed ester of pentaerythritol with 3,5,5-trimethylhexanoic acid and 2-propylheptanoic acid in molar ratio (3,5,5-trimethylhexanoic acid/2-propylheptanoic acid) of 19/81 (Mixed Ester 5)

Mixed Ester 5 was obtained in the same manner as in Example 1, except that the molar ratio of pentaerythritol, 3,5,5-trimethylhexanoic acid, and 2-propylheptanoic acid (pentaerythritol/3,5,5-trimethylhexanoic acid/2-propylheptanoic acid) was changed to 1/0.80/4.00, and the reaction time was changed to 30 hours.

Example 6

Production of mixed ester of pentaerythritol with 3,5,5-trimethylhexanoic acid and 2-propylheptanoic acid in molar ratio (3,5,5-trimethylhexanoic acid/2-propylheptanoic acid) of 16/84 (Mixed Ester 6)

A reactor equipped with a Dean-Stark trap and a dropping funnel was charged with 68 g (0.5 mol) of pentaerythritol (manufactured by Koei Perstorp, Co., Ltd.) and 331 g (1.9 mol) of 2-propylheptanoic acid (see the above production example). The mixture was degassed by nitrogen bubbling at room temperature for 30 minutes with stirring under a reduced pressure of 20 kPa.

The mixture was stirred at 180 to 230° C. for 7 hours with nitrogen bubbling under atmospheric pressure. After the addition of 76 g (0.5 mol) of 3,5,5-trimethylhexanoic acid (manufactured by KH Neochem Co., Ltd.) from the dropping funnel, the mixture was stirred at 230° C. for 11 hours. The total reaction time was 18 hours.

After completion of the reaction, the subsequent operations (removal of unreacted carboxylic acids, washing with alkaline aqueous solution, washing with water, drying, adsorption with adsorbent and activated carbon, and filtration) were performed in the same manner as in Example 1 to obtain 291 g of Mixed Ester 6.

Example 7

Production of mixed ester of pentaerythritol and dipentaerythritol in molar ratio (pentaerythritol/dipentaerythritol) of 90/10 with 3,5,5-trimethylhexanoic acid and 2-propylheptanoic acid in molar ratio (3,5,5-trimethylhexanoic acid/2-propylheptanoic acid) of 56/44 (Mixed Ester 7)

Mixed Ester 7 was obtained in the same manner as in Example 1, except that a mixed alcohol prepared by mixing pentaerythritol (manufactured by Koei Perstorp, Co., Ltd.) and dipentaerythritol (manufactured by Koei Perstorp, Co., Ltd.) was used instead of pentaerythritol, the molar ratio of pentaerythritol, dipentaerythritol, 3,5,5-trimethylhexanoic acid, and 2-propylheptanoic acid (pentaerythritol/dipentaerythritol/3,5,5-trimethylhexanoic acid/2-propylheptanoic acid) was changed to 1/0.11/2.80/2.80, and the reaction time was changed to 27 hours.

Example 8

Production of mixed ester of pentaerythritol and dipentaerythritol in molar ratio (pentaerythritol/dipentaerythritol) of 80/20 with 3,5,5-trimethylhexanoic acid and 2-propylheptanoic acid in molar ratio (3,5,5-trimethylhexanoic acid/2-propylheptanoic acid) of 30/70 (Mixed Ester 8)

Mixed Ester 8 was obtained in the same manner as in Example 1, except that a mixed alcohol prepared by mixing pentaerythritol (manufactured by Koei Perstorp, Co., Ltd.) and dipentaerythritol (manufactured by Koei Perstorp, Co., Ltd.) was used instead of pentaerythritol, the molar ratio of pentaerythritol, dipentaerythritol, 3,5,5-trimethylhexanoic acid, and 2-propylheptanoic acid (pentaerythritol/dipentaerythritol/3,5,5-trimethylhexanoic acid/2-propylheptanoic acid) was changed to 1/0.25/1.85/4.75, and the reaction time was changed to 43 hours.

Comparative Example 1

Production of ester of 3,5,5-trimethylhexanoic acid and pentaerythritol (Ester A)

Ester A was obtained in the same manner as in Example 1, except that only 3,5,5-trimethylhexanoic acid was used as the carboxylic acid, the molar ratio of pentaerythritol to 3,5,5-trimethylhexanoic acid (pentaerythritol/3,5,5-trimethylhexanoic acid) was changed to 1/4.80, and the reaction time was changed to 9 hours.

Comparative Example 2

Production of ester of 2-propylheptanoic acid and pentaerythritol (Ester B)

Ester B was obtained in the same manner as in Example 1, except that only 2-propylheptanoic acid was used as the carboxylic acid, the molar ratio of pentaerythritol to 2-propylheptanoic acid (pentaerythritol/2-propylheptanoic acid) was changed to 1/4.80, and the reaction time was changed to 31 hours.

Comparative Example 3

Production of mixed ester of pentaerythritol with 2-ethylhexanoic acid and 3,5,5-trimethylhexanoic acid in molar ratio (2-ethylhexanoic acid/3,5,5-trimethylhexanoic acid) of 50/50 (Mixed Ester C)

Mixed Ester C was obtained in the same manner as in Example 1, except that 2-ethylhexanoic acid (manufactured by KH Neochem Co., Ltd.) was used instead of 2-propylheptanoic acid, the molar ratio of pentaerythritol, 2-ethylhexanoic acid, and 3,5,5-trimethylhexanoic acid (pentaerythritol/2-ethylhexanoic acid/3,5,5-trimethylhexanoic acid) was changed to 1/2.69/2.11, and the reaction time was changed to 32 hours.

Test Example 1

Measurement of Kinematic Viscosity

The kinematic viscosity of the mixed esters and the esters (Mixed Esters 1 to 8, Ester A, Ester B, and Mixed Ester C) at 40° C. and 100° C. was measured in accordance with the method specified in JIS K 2283:2000 using a Cannon-Fenske viscometer. The viscosity index was calculated in accordance with the method specified in JIS K 2283:2000. The results are shown below and in Tables 1 and 2.

Test Example 2

Measurement of Two-Phase Separation Temperature (Evaluation of Miscibility)

The two-phase separation temperature of the mixed esters and the esters (Mixed Esters 1 to 8, Ester A, and Ester B) was measured in accordance with the method specified in JIS K 2211:2009.

[Evaluation of Miscibility with HFO-1234yf]

A pressure-resistant glass tube was charged with 0.4 g of the mixed ester or the ester (Mixed ester 1 to 8, Ester A, or Ester B) and 3.6 g of HFO-1234yf (manufactured by Honeywell International, Inc.), and the mixture was cooled from 30° C. at a rate of 0.5° C./min. A temperature at which the mixture was separated into two phases, or became cloudy, was determined to be the two-phase separation temperature. The results are shown in Tables 1 and 2.

[Evaluation of Miscibility with HFO-1234ze/HFC-32 (Weight Ratio: 60/40)]

1) Preparation of Mixed Refrigerant

A pressure vessel was charged with HFO-1234ze (manufactured by Honeywell International, Inc.) and HFC-32 (manufactured by Daikin Industries, Ltd.) in a weight ratio (HFO-1234ze/HFC-32) of 60/40 to prepare a mixed refrigerant. The liquid phase of the mixed refrigerant was collected from the pressure vessel, and used for the following measurement of the two-phase separation temperature.

2) Measurement of Two-Phase Separation Temperature

A pressure-resistant glass tube was charged with 0.4 g of the mixed ester or the ester (Mixed Ester 1 to 8, Ester A, or Ester B) and 3.6 g of the mixed refrigerant, and the mixture was cooled from 30° C. at a rate of 0.5° C./min. A temperature at which the mixture was separated into two phases, or became cloudy, was determined to be the two-phase separation temperature. The results are shown in Tables 1 and 2.

[Evaluation of Miscibility with HFO-1234ze]

A pressure-resistant glass tube was charged with 0.4 g of the mixed ester (Mixed Ester 2, 4, or 8) and 3.6 g of HFO-1234ze (manufactured by Honeywell International, Inc.), and the mixture was cooled from 30° C. at a rate of 0.5° C./min. A temperature at which the mixture was separated into two phases, or became cloudy, was determined to be the two-phase separation temperature. The results are shown below.

Test Example 3

Determination of Presence or Absence of Solidification/Precipitation at −20° C. (Evaluation of Low-Temperature Properties)

1.0 g of the mixed ester or the ester (Mixed Ester 1 to 8, Ester A, or Ester B) was put in a glass vessel, and allowed to stand for 24 hours in a thermostat container set at −20° C. When 24 hours had elapsed, the presence or absence of solidification/precipitation was determined by visual observation. A case where solidification/precipitation was not observed was evaluated as "Acceptable", and a case where solidification/precipitation was observed was evaluated as "Unacceptable". The results are shown in Tables 1 and 2.

Test Example 4

Measurement of RBOT Life (Evaluation of Oxidation-Hydrolysis Stability and Oxidation Stability)

[Condition 1]

An oxidation stability test was performed in accordance with the method specified in JIS K 2514-1996 using a rotating bomb oxidation tester "RBOT-02" (manufactured by Rigo Co., Ltd.). A pressure vessel was charged with 49.50 g of the mixed ester or the ester (Mixed Ester 1 to 8, Ester A, or Ester B), 0.25 g of 4,4'-methylenebis(2,6-di-tert-butylphenol) (manufactured by Tokyo Chemical Industry Co., Ltd.), 0.25 g of IRGANOX L57 (manufactured by Ciba Specialty Chemicals), 5 mL of water, and an electrolytic copper wire (diameter: 1.6 mm, length: 3 m) that was polished using sandpaper #400, and was pressurized to 620 kPa by oxygen. The pressure vessel was placed in a thermostat bath at 150° C., and rotated at 100 rpm to start the test. A point at which a pressure drop of 175 kPa after a pressure of the pressure vessel achieved maximum was determined as the end point. The period of time from the start of the test to the end point was obtained (RBOT life). The results are shown in Tables 1 and 2. In Tables 1 and 2, a longer RBOT life (Condition 1) indicates that the mixed ester or the ester had better oxidation-hydrolysis stability.

[Condition 2]

An operation was performed in the same manner as described above (see "Condition 1"), except that 4,4'-methylenebis(2,6-di-tert-butylphenol), IRGANOX L57, and water were not used, and the period of time (RBOT life) was determined. The results are shown in Tables 1 and 2. In Tables 1 and 2, a long RBOT life (Condition 2) indicates that the mixed ester or the ester had excellent oxidation stability.

Test Example 5

Measurement of Volume Resistivity (Evaluation of Electrical Insulating Properties)

The volume resistivity of Mixed Esters 1 to 8 at 30° C. was measured in accordance with the method specified in JIS C 2101-1999 using a digital ultra-high resistance/micro current meter "R8340A" (manufactured by Advantest Corporation) and a liquid electrode "DAC-OBE-2" (manufactured by Soken Electric Co, Ltd.). The results are shown below.

Test Example 6

Measurement of Pour Point

The pour point of Mixed Esters 1 to 8 was measured in accordance with the method specified in JIS K 2269-1987 using an automatic pour point measurement system "RPC-01CML" (manufactured by Rigo Co., Ltd.). The results are shown below.

Test Example 7

Measurement of Wear Scar Diameter (Evaluation of Antiwear Properties)

0.45 g of tricresyl phosphate (manufactured by Tokyo Chemical Industry Co., Ltd.) was added to 14.55 g of the mixed ester (Mixed Ester 1 to 8 or Mixed Ester C) to prepare a refrigerant oil. The refrigerant oil was subjected to a wear test using a shell four-ball wear tester (manufactured by Shinko Engineering Co., Ltd.) (load: 100 N, rotating speed: 1200 rpm, duration: 60 minutes, temperature: 75° C., test piece (test ball (SUJ-2)) to measure the wear scar diameter. The average value of the wear scar diameters on the three stationary balls in both vertical and horizontal directions was taken as the wear scar diameter. The results are shown below. A smaller wear scar diameter indicates that the refrigerant oil had better antiwear properties.

Test Example 8

Measurement of Weight Loss Temperature (Evaluation of Thermal Stability)

The 5% weight loss temperature of Mixed Esters 1 to 8 was measured under the following conditions using a thermogravimetry-differential thermal analyzer "Tg-DTA 6200" (manufactured by Seiko Instruments Inc.). The results are shown below. Measurement temperature: 40 to 420° C., temperature increase rate: 10° C./min, atmosphere: nitrogen flow (300 mL/min), sample container: aluminum container (15 µL (open)), sample volume: 3 mg

TABLE 1

|  |  | Mixed Ester 1 (Example 1) | Mixed Ester 2 (Example 2) | Mixed Ester 3 (Example 3) | Mixed Ester 4 (Example 4) | Mixed Ester 5 (Example 5) | Mixed Ester 6 (Example 6) | Mixed Ester 7 (Example 7) | Mixed Ester 8 (Example 8) |
|---|---|---|---|---|---|---|---|---|---|
| Ratio of alcohol (mol %) | Pentaerythritol | 100 | 100 | 100 | 100 | 100 | 100 | 90 | 80 |
|  | Dipentaerythritol | — | — | — | — | — | — | 10 | 20 |
| Ratio of carboxylic acid (mol %) | 3,5,5-Trimethyl-hexanoic acid | 90 | 77 | 50 | 34 | 19 | 16 | 56 | 30 |
|  | 2-Propylheptanoic acid | 10 | 23 | 50 | 66 | 81 | 84 | 44 | 70 |
| Kinematic viscosity ($mm^2$/sec) | 40° C. | 108.4 | 90.4 | 73.2 | 65.8 | 60.8 | 60.0 | 89.3 | 84.4 |
|  | 100° C. | 11.0 | 10.2 | 9.0 | 8.5 | 8.0 | 8.1 | 10.3 | 10.0 |
| Viscosity index |  | 82 | 92 | 95 | 98 | 98 | 100 | 95 | 98 |
| Two-phase separation temperature (° C.) | HFO-1234yf | <−50 | <−50 | −39 | −29 | −17 | −17 | −41 | −20 |
|  | HFO-1234ze/HFC-32 (Weight ratio; 60/40) | <−50 | <−50 | −31 | −24 | −17 | −15 | −34 | −15 |
| Low-temperature properties |  | Acceptable | Acceptable | Acceptable | Acceptable | Acceptable | Acceptable | Acceptable | Acceptable |
| RBOT life (min) | Condition 1 | 2070 | 2320 | 2320 | 2340 | 2330 | 2360 | 2110 | 3060 |
|  | Condition 2 | 171 | 95 | 83 | 77 | 68 | 65 | 84 | 66 |

TABLE 2

|  |  | Ester A (Comparative Example 1) | Ester B (Comparative Example 2) |
|---|---|---|---|
| Ratio of alcohol (mol %) | Pentaerythritol | 100 | 100 |
|  | Dipentaerythritol | — | — |
| Ratio of carbioxylic acid (mol %) | 3,5,5-Trimethylhexanoic acid | 100 | — |
|  | 2-Propylheptanoic acid | — | 100 |
| Kinematic viscosity ($mm^2$/sec) | 40° C. | 113.3 | 55.0 |
|  | 100° C. | 11.6 | 7.9 |
| Viscosity index |  | 87 | 110 |
| Two-phase separation temperature (° C.) | HFO-1234yf | <−50 | −9 |
|  | HFO-1234ze/HFC-32 (Weight ratio; 60/40) | <−50 | −8 |
| Low-temperature properties |  | Unacceptable | Acceptable |
| RBOT life (min) | Condition 1 | 1740 | 2420 |
|  | Condition 2 | 222 | 60 |

As shown in Table 1, Mixed Esters 1 to 8 had kinematic viscosity at 40° C. of 60.0 to 108.4 $mm^2$/sec, a two-phase separation temperature of −17° C. or less when mixed with HFO-1234yf, and a two-phase separation temperature of −15° C. or less when mixed with HFO-1234ze/HFC-32 (weight ratio: 60/40); did not show solidification/precipitation at −20° C.; had a RBOT life of 2070 minutes or more under Condition 1; and had a RBOT life of 65 minutes or more under Condition 2. Mixed Esters 2, 4, and 8 had a two-phase separation temperature of −50° C. or less when mixed with HFO-1234ze. It was thus confirmed that Mixed Esters 1 to 8 had excellent miscibility with a refrigerant that comprises fluoropropene, excellent low-temperature properties, excellent oxidation-hydrolysis stability, and excellent oxidation stability in a well-balanced manner while having the viscosity within the range required for a refrigerant oil. As shown in Table 2, Ester A had poor low-temperature properties, and Ester B had poor miscibility with HFO-1234yf and HFO-1234ze/HFC-32 (weight ratio: 60/40). Esters A and B had poorly-balanced properties as compared with Mixed Esters 1 to 8.

In Test Example 1, Mixed Ester C had kinematic viscosity at 40° C. of 67.0 $mm^2$/sec, kinematic viscosity at 100° C. of 8.3 $mm^2$/sec, and viscosity index of 92.

In Test Example 5, Mixed Esters 1 to 8 had a volume resistivity (30° C.) of $1 \times 10^{16}$ Ω·cm or more. It was thus confirmed that the mixed esters according to the invention had sufficient electrical insulating properties.

In Test Example 6, Mixed Esters 1 to 8 had a pour point of −37.5° C. or less. It was thus confirmed that the mixed esters according to the invention had sufficient low-temperature fluidity.

In Test Example 7, the wear scar diameter of the refrigerant oils consisting of the mixed ester (Mixed Ester 1 to 8) and tricresyl phosphate was 0.23 mm or less. The wear scar diameter of the refrigerant oil consisting of Mixed Ester C and tricresyl phosphate was 0.37 mm. It was thus confirmed that the mixed esters according to the invention provided excellent antiwear properties to the refrigerant oil according to the invention.

In Test Example 8, Mixed Esters 1 to 8 had a 5% weight loss temperature of 260° C. or more. It was thus confirmed that the mixed esters according to the invention had sufficient thermal stability.

INDUSTRIAL APPLICABILITY

The invention thus provides a mixed ester that exhibits excellent properties (e.g., miscibility with a refrigerant that comprises fluoropropene, low-temperature properties, oxidation stability, oxidation-hydrolysis stability, and lubricity) in a well-balanced manner while having the viscosity within the range required for a refrigerant oil, and may be used in an industrial lubricant (e.g., refrigerant oil) and the like.

The invention claimed is:

1. A mixed ester of pentaerythritol or a mixed polyhydric alcohol and carboxylic acids; the mixed polyhydric alcohol consisting of pentaerythritol and dipentaerythritol represented by the following formula (I), and the carboxylic acids comprising 3,5,5-trimethylhexanoic acid and 2-propylheptanoic acid

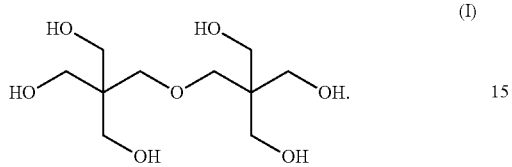

(I)

2. The mixed ester according to claim 1, wherein the carboxylic acids consist of 3,5,5-trimethylhexanoic acid and 2-propylheptanoic acid.

3. The mixed ester according to claim 1, wherein the carboxylic acids comprise 3,5,5-trimethylhexanoic acid and 2-propylheptanoic acid in a molar ratio of 90/10 to 10/90.

4. The mixed ester according to claim 1, wherein the polyhydric alcohol that forms the mixed ester in pentaerythritol.

5. A refrigerant oil comprising the mixed ester according to claim 1.

6. A working fluid composition for refrigerator comprising the refrigerant oil according to claim 5 and a refrigerant.

* * * * *